United States Patent
Searle

(10) Patent No.: US 6,593,506 B1
(45) Date of Patent: Jul. 15, 2003

(54) OLEFIN RECOVERY IN A POLYOLEFIN PRODUCTION PROCESS

(75) Inventor: Ronald G. Searle, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/689,363

(22) Filed: Oct. 12, 2000

(51) Int. Cl.$^7$ .............................. C07C 1/00; C07C 1/20
(52) U.S. Cl. .................... 585/639; 585/638; 585/640
(58) Field of Search .................... 585/638, 639, 585/640

(56) References Cited

U.S. PATENT DOCUMENTS

| | | | |
|---|---|---|---|
| 2,936,303 A | 5/1960 | Goins | 260/93.7 |
| 3,258,455 A | 6/1966 | Natta et al. | 260/93.7 |
| 3,305,538 A | 2/1967 | Natta et al. | 260/93.7 |
| 3,364,190 A | 1/1968 | Emrick | 260/93.7 |
| 3,450,777 A | 6/1969 | Mizutani et al. | 260/641 |
| 3,452,106 A | 6/1969 | Sato et al. | 260/641 |
| 3,635,803 A | 1/1972 | Binns et al. | 204/80 |
| 3,645,992 A | 2/1972 | Elston | 260/80.78 |
| 3,758,615 A | 9/1973 | Izumi et al. | 260/641 |
| 3,957,448 A | 5/1976 | Shepard et al. | 23/288 R |
| 3,965,083 A | 6/1976 | Jezl et al. | 526/65 |
| 3,971,768 A | 7/1976 | Peters et al. | 526/68 |
| 4,008,290 A | 2/1977 | Ward | 260/672 T |
| 4,012,456 A | 3/1977 | Chaplits | 260/677 |
| 4,041,095 A | 8/1977 | Kuo | 260/676 R |
| 4,046,822 A | 9/1977 | Severino | 260/659 A |

(List continued on next page.)

FOREIGN PATENT DOCUMENTS

| | | |
|---|---|---|
| EP | 0 012 147 | 3/1979 |
| EP | 0 533 452 | 9/1992 |
| EP | 0 560 312 | 3/1993 |
| EP | 0 574 821 | 6/1993 |
| EP | 0 612 753 | 6/1999 |
| EP | 0 933 345 | 8/1999 |
| GB | 2039905 | 1/1979 |
| WO | WO 92/12184 | 7/1992 |
| WO | WO 93/24533 | 12/1993 |
| WO | WO 98/29464 | 7/1998 |

OTHER PUBLICATIONS

*MTO—has its time come?*, Nitrogen & Methanol, No. 246, (Jul.–Aug. 2000).
*New route to low–density polyethylene*, Chemical Engineering, pp. 80–85 (Dec. 3, 1979).
Barger et al., *Converting Natural Gas to Ethylene and Propylene by the UOP/Hydro MTO Process*, 12$^{th}$ International Zeolite Conference Materials Research Society p. 567–573 (1999).
Blackwell et al., *Solid–State NMR of Silicoaluminophosphate Molecular Sieves and Aluminophosphate Materials*, J. Phys. Chem., 92, pp. 3965–3970 (1988).
Hatch & Matar, *From Hydrocarbons to Petrochemicals*, Chapter 9 and pp. 106–119, 137–140, 172–179.
Karol, Fredrick J., *The Polyethylene Revolution*, Chemtech, pp. 222–228, (Apr. 1983).
Kirk–Othmer Encyclopedia of Chemical Technology, 4th edition, vol. 9, John Wiley & Sons, pp. 894–899, (1996).
Kirk–Othmer Encyclopedia of Chemical Technology, 4th edition, vol. 20, John Wiley & Sons, pp. 249–271 (1996).

*Primary Examiner*—Walter D. Griffin
*Assistant Examiner*—Tam Minh Nguyen
(74) *Attorney, Agent, or Firm*—Paul T. Lavoie

(57) ABSTRACT

Disclosed is a method of recovering olefin from purge streams in a polyolefin production process. The method includes reacting a purge stream containing olefin and impurities with water in the presence of a hydrating catalyst to produce an alcohol containing stream. The impurities can include methane, ethane, butylenes, and hydrogen. The alcohol containing stream can be used to produce olefins in an oxygenate to olefin production process.

7 Claims, 1 Drawing Sheet

U.S. PATENT DOCUMENTS

| | | | | |
|---|---|---|---|---|
| 4,068,136 A | 1/1978 | Minami | | 307/353 |
| 4,076,698 A | 2/1978 | Anderson et al. | | 526/348.6 |
| 4,101,289 A | 7/1978 | Jezl et al. | | 23/288 E |
| 4,172,099 A | 10/1979 | Severino | | 260/660 |
| 4,187,278 A | 2/1980 | Clifford | | 422/132 |
| 4,243,691 A | 1/1981 | Mohlenkamp, Jr. et al. | | 426/649 |
| 4,244,892 A | 1/1981 | Guseinov et al. | | 570/223 |
| 4,263,212 A | 4/1981 | Hong et al. | | 260/347.5 |
| 4,287,091 A | 9/1981 | Selman | | 252/429 |
| 4,302,565 A | 11/1981 | Goeke et al. | | 526/88 |
| 4,310,440 A | 1/1982 | Wilson et al. | | 252/435 |
| 4,318,800 A | 3/1982 | Woebcke et al. | | 208/127 |
| 4,340,769 A | 7/1982 | Brandes et al. | | 568/899 |
| 4,343,957 A | 8/1982 | Sartorio et al. | | 585/449 |
| 4,404,095 A | 9/1983 | Haddad et al. | | 208/161 |
| 4,419,221 A | 12/1983 | Castagnos, Jr. et al. | | 208/113 |
| 4,426,449 A | 1/1984 | Geigert et al. | | 435/155 |
| 4,433,188 A | 2/1984 | Hoelderich et al. | | 585/640 |
| 4,440,871 A | 4/1984 | Lok et al. | | 502/214 |
| 4,463,207 A | 7/1984 | Johnson | | 585/462 |
| 4,471,147 A | 9/1984 | Owen et al. | | 585/519 |
| 4,474,647 A | 10/1984 | Asselineau et al. | | 203/49 |
| 4,482,687 A | 11/1984 | Noshay et al. | | 526/125 |
| 4,499,327 A | 2/1985 | Kaiser | | 585/640 |
| 4,504,691 A | 3/1985 | Hsia et al. | | 585/519 |
| 4,508,842 A | 4/1985 | Beran et al. | | 502/112 |
| 4,521,631 A | 6/1985 | Nishimura et al. | | 564/478 |
| 4,524,229 A | 6/1985 | Johnson | | 585/463 |
| 4,554,392 A | 11/1985 | Leuck et al. | | 570/254 |
| 4,558,167 A | 12/1985 | Riegel et al. | | 570/238 |
| 4,567,029 A | 1/1986 | Wilson et al. | | 423/306 |
| 4,623,704 A | 11/1986 | Dembicki et al. | | 526/68 |
| 4,629,484 A | 12/1986 | Kister | | 62/29 |
| 4,659,685 A | 4/1987 | Coleman, III et al. | | 502/113 |
| 4,677,242 A | 6/1987 | Kaiser | | 585/638 |
| 4,677,243 A | 6/1987 | Kaiser | | 585/638 |
| 4,710,482 A | 12/1987 | Job | | 502/127 |
| 4,721,824 A | 1/1988 | McWilliams et al. | | 585/448 |
| 4,749,817 A | 6/1988 | George et al. | | 570/204 |
| 4,752,651 A | 6/1988 | Kaiser | | 585/640 |
| 4,861,743 A | 8/1989 | Flank et al. | | 502/214 |
| 4,861,939 A | 8/1989 | Debras et al. | | 585/820 |
| 4,956,426 A | 9/1990 | Ardell et al. | | 526/60 |
| 4,992,608 A | 2/1991 | Cavani et al. | | 585/467 |
| 5,019,143 A | 5/1991 | Mehrta | | 62/17 |
| 5,055,627 A | 10/1991 | Smith, Jr. et al. | | 585/467 |
| 5,068,475 A | 11/1991 | Schmidhammer et al. | | 570/262 |
| 5,096,684 A | 3/1992 | Guth et al. | | 423/306 |
| 5,102,841 A | 4/1992 | Cann et al. | | 502/112 |
| 5,126,308 A | 6/1992 | Barger et al. | | 502/214 |
| 5,144,090 A | 9/1992 | Honda et al. | | 568/476 |
| 5,183,936 A | 2/1993 | Etzkorn et al. | | 562/532 |
| 5,198,578 A | 3/1993 | Etzkorn et al. | | 562/532 |
| 5,235,088 A | 8/1993 | Paparizos et al. | | 558/324 |
| 5,238,892 A | 8/1993 | Chang | | 502/111 |
| 5,240,894 A | 8/1993 | Burkhardt et al. | | 502/108 |
| 5,243,115 A | 9/1993 | Smith, Jr. et al. | | 585/446 |
| 5,243,116 A | 9/1993 | Lee et al. | | 585/467 |
| 5,258,543 A | 11/1993 | Suresh et al. | | 558/325 |
| 5,262,575 A | 11/1993 | Dianis | | 570/235 |
| 5,262,576 A | 11/1993 | Smith, Jr. | | 585/447 |
| 5,274,138 A | 12/1993 | Keating et al. | | 549/529 |
| 5,280,074 A | 1/1994 | Schreck et al. | | 525/240 |
| 5,288,473 A | 2/1994 | Shaw et al. | | 423/237 |
| 5,300,707 A | 4/1994 | Caillod et al. | | 568/480 |
| 5,326,465 A | 7/1994 | Yongqing et al. | | 208/120 |
| 5,326,929 A | 7/1994 | Mehra et al. | | 585/809 |
| 5,349,072 A | 9/1994 | Preston et al. | | 549/529 |
| 5,364,915 A | 11/1994 | Benham et al. | | 526/105 |
| 5,432,243 A | 7/1995 | Bodart | | 526/68 |
| 5,504,166 A | 4/1996 | Buchelli et al. | | 526/60 |
| 5,523,502 A | 6/1996 | Rubin | | 585/324 |
| 5,608,123 A * | 3/1997 | Inoue et al. | | 568/899 |
| 5,609,734 A | 3/1997 | Streicher et al. | | 203/39 |
| 5,681,908 A | 10/1997 | Mehra et al. | | 526/68 |
| 5,684,097 A | 11/1997 | Palmroos et al. | | 526/64 |
| 5,689,032 A | 11/1997 | Krause et al. | | 585/802 |
| 5,714,662 A | 2/1998 | Vora et al. | | 585/640 |
| 5,741,350 A | 4/1998 | Rowles et al. | | 95/42 |
| 5,744,680 A | 4/1998 | Mulvaney, III et al. | | 585/640 |
| 5,811,621 A | 9/1998 | Van Dijk | | 585/639 |
| 5,817,906 A | 10/1998 | Marker et al. | | 585/640 |
| 5,892,079 A | 4/1999 | Wilson, Jr. | | 556/11 |
| 5,907,076 A | 5/1999 | Ou et al. | | 585/800 |
| 5,914,433 A | 6/1999 | Marker | | 585/313 |
| 5,960,643 A | 10/1999 | Kuechler et al. | | 62/620 |
| 5,981,818 A | 11/1999 | Purvis et al. | | 585/519 |
| 5,990,369 A | 11/1999 | Barger et al. | | 585/640 |
| 6,049,017 A | 4/2000 | Vora et al. | | 585/324 |
| 6,066,701 A | 5/2000 | Koveal et al. | | 526/64 |
| 6,069,288 A | 5/2000 | Ou et al. | | 585/800 |
| 6,121,503 A | 9/2000 | Janssen et al. | | 585/640 |
| 6,121,504 A | 9/2000 | Kuechler et al. | | 585/640 |
| 6,137,022 A * | 10/2000 | Kuechler et al. | | 585/638 |
| 6,173,584 B1 | 1/2001 | Agrawal | | 62/620 |

\* cited by examiner

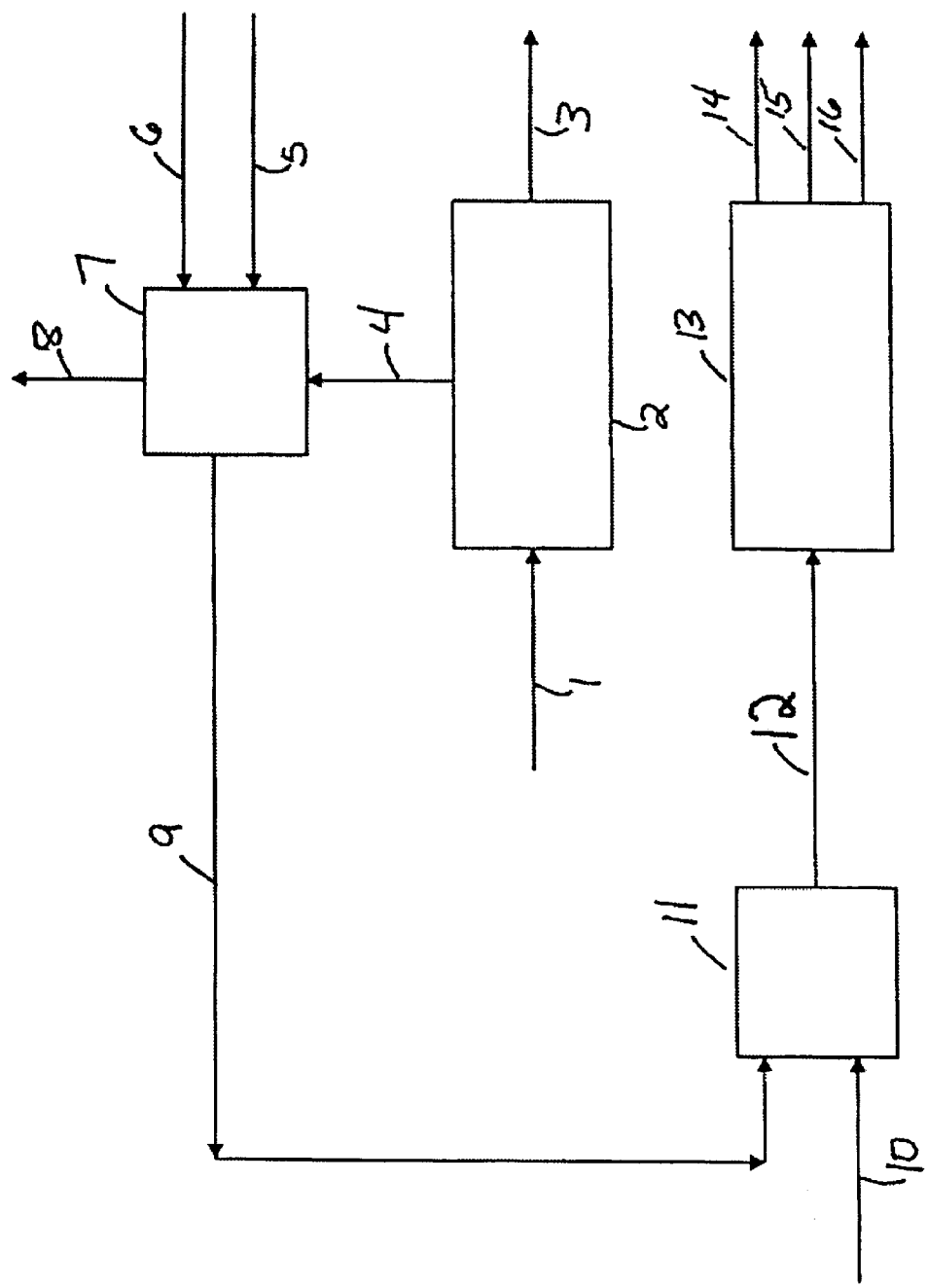
Figure

OLEFIN RECOVERY IN A POLYOLEFIN PRODUCTION PROCESS

FIELD OF INVENTION

This invention relates to recovering ethylene from a polyethylene production process. In particular this invention relates to recovering ethylene from a polyethylene production process, converting the ethylene to ethanol, and converting the ethanol to olefin.

BACKGROUND OF THE INVENTION

Ethylene is one of the most important raw materials for organic chemical production. The present world demand for ethylene is about 80 million tons per year, with 57% of this demand attributable to the polyethylene industry. The preparation of polyethylene typically requires a highly purified ethylene raw material. An ethylene monomer concentration of 99.9 mole % is typically required for polyethylene production.

High purity olefin monomer is required throughout most polyolefin polymerization processes. During the typical olefin polymerization process, olefin monomer is charged to a reactor where some of the olefin monomer reacts to form polyolefins. Unreacted olefin monomer is recycled back into the reactor. Impurities in the monomer, such as methane, ethane, butylenes, and hydrogen can build up in the recycle stream requiring that a percentage of the recycle stream be purged.

The purge stream contains a high percentage of valuable olefin monomer, and recovery of this monomer is important for both economical and environmental reasons. However, the separation of impurities from light olefins such as ethylene and propylene typically requires expensive cryogenic distillation techniques.

Alternative techniques that do not require cryogenic temperatures have been explored. Dembicki et al. U.S. Pat. No. 4,623,704 discloses the use of membranes to recover the ethylene enriched gas in a polyethylene process. Mehra et al. U.S. Pat. No. 5,681,908 discloses an absorption process for the recovery of monomers in olefin polymerization processes.

The U.S. Environmental Protection Agency currently has a program to develop a process for recovering ethylene without the need for low process temperatures and with higher selectivities for purge stream impurities than offered by polymeric membranes.

Therefore, a need exists, for recovery of olefin, e.g., ethylene and propylene, during the polyolefin manufacturing process in order to reduce the loss of olefins. In particular, it is highly desirable to recover olefins in a highly pure and cost effective manner.

SUMMARY OF THE INVENTION

In order to recover olefins from a purge stream in a polyolefin production process, this invention provides for hydrating olefins in a purge stream to produce alcohols. The alcohol, after being separated from impurities in the purge stream, can then be used to make olefin products.

In one embodiment, the invention provides a method of purifying an olefin containing purge stream. The method comprises reacting a purge stream containing olefin and impurities with water in the presence of a hydrating catalyst to produce an alcohol containing stream. The alcohol from the alcohol containing stream is contacted with an olefin forming catalyst to form an olefin product stream.

Preferably, the impurities in the purge stream comprise at least one compound selected from the group consisting of methane, ethane, butylenes, and hydrogen. Preferably, the hydrating catalyst is a supported phosphoric acid catalyst. Preferably, the olefin forming catalyst is a silicoaluminophosphate molecular sieve catalyst. Preferably, the alcohol containing stream contains ethanol or propanol. Preferably, the reaction of a purge stream containing olefin and impurities with water in the presence of a hydrating catalyst is performed at a temperature of 180° C. to 300° C. and a pressure of 350 psig to 1000 psig.

In another embodiment, the invention provides a method of producing olefins from oxygenates. The method comprises mixing an oxygenate feed stream with an alcohol containing stream, the alcohol containing stream produced from a purge stream in a polyolefin production process. The mixed oxygenate and alcohol feed stream is converted in the presence of an olefin forming catalyst into an olefin product stream.

This invention will be better understood by reference to the Detailed Description of the Invention when taken together with the attached FIGURE and the appended claims.

BRIEF DESCRIPTION OF THE DRAWINGS

The FIGURE shows a flow diagram of the process of the invention.

DETAILED DESCRIPTION OF THE INVENTION

In a continuous olefin polymerization process, olefin monomer is fed into a reactor in the presence of a catalyst or free-radical initiator to produce polyolefin. A monomer recycle stream is often required because of incomplete conversion of monomer into polymer in the reactor. Conventionally, a percentage of the recycle stream is purged from the recycle stream to minimize accumulation of feedstream impurities such as methane, ethane, butylenes, and hydrogen. Most often this purge stream is used as fuel gas, resulting in a significant loss of olefin monomer and possibly process pollution. The subject invention allows for the recovery of olefin from the purge stream without the need for cryogenic distillation or polymeric membranes.

The purge stream, which contains valuable olefin, is combined with water and passed over a hydrating catalyst. This procedure converts the olefins in the purge stream into alcohols. The alcohols having a higher condensation temperature than the associated olefins can more easily be separated from the impurities in the purge stream with conventional separation techniques.

The olefins ethylene and propylene have boiling points of −103.7° C. and −47.6° C. respectfully. Impurities in the purge stream, for example methane, often have boiling points lower than olefins and therefore, require even lower temperatures to condense than the olefins. Consequently, to remove methane from olefin containing streams by conventional distillation techniques typically requires that the olefins be condensed, which involves cryogenic temperatures.

Alcohols have much higher boiling point temperatures than their associated olefins. For example, ethanol and 2-propanol, have boiling point temperatures of 78.5° C. and 87° C. respectfully and can be condensed and separated from impurities without the need for cryogenic temperatures by conventional techniques. After the impurities are separated from the alcohols, the alcohols can be reconverted into pure olefin monomer by using them as a feed in an oxygenate to olefins reaction process.

Any olefin polymerization process that produces a purge stream containing olefin monomer and impurities may be practiced as part of the present invention.

Processes for forming polyolefins from olefins are known in the art. Preferred catalytic processes are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. For polyethylene manufacturing, the preferred temperature of operation is between 50° C. and 240° C. and the reaction can be carried out at low, medium or high pressure, being anywhere from 1 bar to 200 bars. For processes carried out in solution, an inert diluent can be used, and the preferred operating pressure range is between 10 bars and 150 bars, with a preferred temperature range of between 120° C. and 230° C. For gas phase processes, the temperature generally can be from 60° C. to 160° C., and that the operating pressure be from 5 bars to 50 bars.

Any conventional reactor type may be used for the polymerization process of the present invention including fluid bed reactors, fixed bed reactors, slurry reactors, or linear flow reactors. The use of a fluid bed reactor is described in U.S. Pat. No. 4,482,687, the reactor and catalyst description expressly being incorporated herein. The use of a linear flow loop type reactor is disclosed in U.S. Pat. No. 5,684,097, the reactor and catalyst description being expressly incorporated herein.

In a fluid bed process, solid polymer powder is maintained in a fluidized state by passing a stream of reaction gas up from the base of a reactor, where the reaction gas comprises olefin monomer. The reaction gas is withdrawn from the top of the reactor cooled and then recycled back to the base of the reactor. Solid polymer is removed as it builds up at the base of the reactor. A high rate of reaction gas recycle is typically required to achieve fluidization. Generally the recycle rate is about 50 times the rate of a stream of new olefin gas feed to the column. The new olefin gas stream is fed to the column at a rate equal to the withdraw of polyolefin product and any purge stream.

A loop reactor is a preferred form of a linear flow reactor. In a loop reactor, long straight lengths of tubing are interjected with short bends forming a loop. Monomer, catalyst, and frequently a solvent are charged into the loop forming a slurry. Polymer formed in the loop is collected in settling legs located at the base of the reactor. Multiple loops may be used with portions of the slurry from the first reactor withdrawn and added to a second loop reactor.

In continuous polymerization processes, monomer recycle is frequently required because of low per-pass conversion. Polyolefins are typically removed as they settle from the reaction stream. As polyolefin is removed from the process stream, new olefin monomer is continuously being added.

New monomer is typically of high purity, approximately 99.9 mol %, but as monomer reacts to form polyolefins impurities build up in monomer that recycles through the reactor. The build up occurs since olefin monomer that is added to the polymerization process is removed as polymer from the polymerization process. The impurities, however, are not removed from the reactor during this process. As a result, during a continuous polymerization process the impurities need to be removed from the reaction process.

Conventionally, the impurities are removed by way of a purge stream, which simply removes a percentage of the olefin monomer recycle. For example, in a conventional continuous process for making low density polyethylene, 1% to 2% of the ethylene monomer is purged from the polyethylene reactors to minimize accumulation of impurities. The process of this invention allows for the recovery of olefin in the purge stream.

The recovery of the olefins from the purge stream is accomplished by hydrating the olefins in the purge stream to convert them into alcohols. In a preferred embodiment, ethylene is hydrated to form ethanol. The hydration of the olefin can be accomplished either by an indirect route, where an intermediate is formed from the olefin prior to the formation of the alcohol, or a direct route, where the olefin is converted directly into alcohol.

A preferred indirect intermediate route consists of passing an olefin gas stream through concentrated sulfuric or phosphoric acid to form an ester. Water is then added to the acid ester mixture and heated to form alcohol.

In the subject invention, it is more preferred to use a direct hydration process. Conventional direct hydration processes can be used in this invention. A preferred direct hydration process is liquid phase hydration, which occurs in the presence of a dissolved tungsten containing catalyst. Two variations of this process are described in U.S. Pat. Nos. 3,758,615 and 3,450,777, the catalyst and process descriptions of each being expressly incorporated herein by reference. A direct hydration process using a pelleted tungsten-containing catalyst can also be used as described in U.S. Pat. No. 3,452,106, the catalyst and process description being expressly incorporated herein by reference.

Another preferred type of direct hydration process is a mixed phase process in which both gas and liquid phase hydrocarbons are present and a cation exchange resin-type catalyst is employed. Ion exchange catalysts are synthetic resins possessing a hydrocarbon skeleton combined with strong mineral acid groups. The use of such a compound in the direct hydration of an aliphatic olefin is described in U.S. Pat. No. 4,340,769, which is incorporated herein by reference.

The gas phase method is also a preferred embodiment of this invention. Gas phase hydration conventionally employs either a liquid co-feed system or an acid loaded on a solid support structure. A preferred acid catalyst comprises phosphoric acid impregnated on an inert support such as celite diatomite. A fixed bed catalyst system which comprises a supported phosphoric acid is known in the art.

In a preferred gas phase embodiment of this invention, a purge stream containing olefins is combined with water, typically in the form of steam, and fed into a fixed bed hydration reactor. The ethanol reactor typically operates at a low conversion per pass to minimize the formation of unwanted by-products. Higher conversions are obtained by the use of recycle streams. It is preferred that the molar ratio of water to entering olefinic hydrocarbon is from 0.5:1 to 40:1. More preferably, this ratio is from 0.5:1 to 20:1. Excess water need not be removed following the hydration process, as some or all of the water can be used as a diluent in the oxygenate to olefin process.

Catalytic hydration may be conducted over a wide range of conditions. Typically, the olefin containing stream is heated at a temperature of 180° C. to 300° C. and contacted with the phosphoric acid catalyst under pressure of 350 psig to 1000 psig.

Direct hydration is an exothermic reaction. The product stream exiting the reactor comprises a gaseous mixture of steam, alcohols, purge stream impurities, and unreacted olefins. Following the hydration reaction, the gaseous mixture is charged to a scrubber where the steam and alcohols are condensed and removed from the impurities and unreacted olefins. The stream containing the impurities and unreacted olefins may be returned to the reactor for a higher olefin to alcohol conversion.

After the hydration process, the alcohols produced are combined with an oxygenate feed stock to produce a combined oxygenate feed stock. The combined oxygenate feed stock is used to produce olefins. These oxygenates are desirably converted into olefins using a molecular sieve catalyst.

In this invention, a preferred molecular sieve catalyst used to convert the oxygenate feed to olefin is a silicoaluminophosphate (SAPO) molecular sieve catalyst. The molecular sieve comprises a three-dimensional microporous crystal framework structure of $[SiO_2]$, $[AlO_2]$ and $[PO_2]$ corner sharing tetrahedral units. The way Si is incorporated into the structure can be determined by $^{29}Si$ MAS NMR. The desired SAPO molecular sieves will exhibit one or more peaks in the $^{29}Si$ MAS NMR, with a chemical shift δ (Si) in the range of −88 to −96 ppm and with a combined peak area in that range of at least 20% of the total peak area of all peaks with a chemical shift δ (Si) in the range of −88 ppm to −115 ppm, where the δ (Si) chemical shifts refer to external tetramethylsilane (TMS).

It is preferred that the silicoaluminophosphate molecular sieve used in this invention have a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being preferred, and a $Si/Al_2$ ratio of not greater than 0.32 being particularly preferred. A $Si/Al_2$ ratio of not greater than 0.20 is most preferred.

Silicoaluminophosphate molecular sieves are generally classified as being microporous materials having 8, 10, or 12 membered ring structures. These ring structures can have an average pore size ranging from 3.5 to 15 angstroms. Preferred are the small pore SAPO molecular sieves having an average pore size of less than about 5 angstroms, preferably an average pore size of about 3.5 to 5 angstroms, more preferably from 3.5 to 4.2 angstroms. These pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-17, SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an $AlPO_4$ framework. They can have additional elements within the framework, typically have uniform pore dimensions ranging from 3 angstroms to 10 angstroms, and are capable of making size selective separations of molecular species. More than two dozen structure types have been reported, including zeolite topological analogues. Methods for making aluminophosphates are known in the art. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of $MO_2$, $AlO_2$ and $PO_2$ tetrahedral units. These as manufactured structures (which contain template prior to calcination) can be represented by empirical chemical composition, on an anhydrous basis, as:

$$mR: (M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved; "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieves are synthesized by hydrothermal crystallization methods generally known in the art. See, for example, U.S. Pat. Nos. 4,440,871; 4,861,743; 5,096,684; and 5,126,308. A reaction mixture is formed by mixing together reactive silicon, aluminum and phosphorus components, along with at least one template. Generally the mixture is sealed and heated, preferably under autogenous pressure, to a temperature of at least 100° C., preferably from 100° C. to 250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product is formed in solution. It can be recovered by standard means, such as by centrifugation or filtration. The product can also be washed, recovered by the same means, and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from 200° C. to 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The reaction mixture can contain one or more templates. Templates are structure directing or affecting agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, dipropylamine, and mixtures thereof. The tetraethyl ammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of 0.05 cal/g-° C. to 1 cal/g-° C., more preferably from 0.1 cal/g-° C. to 0.8 cal/g-° C., most preferably from 0.1 cal/g-° C. to 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. Preferred molecular sieves which can be combined with a silicoaluminophosphate catalyst include ZSM-5, ZSM-34, erionite, and chabazite.

The catalyst composition preferably comprises 1% to 99%, more preferably 5% to 90%, and most preferably 10% to 80%, by weight of molecular sieve. It is also preferred that the catalyst composition have a particle size of from $20\mu$ to $3,000\mu$, more preferably $30\mu$ to $200\mu$ most preferably $50\mu$ to $150\mu$.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

In this invention, the alcohol from the hydration process can be mixed with oxygenates, preferably methanol and ethanol, and optionally a diluent or a hydrocarbon. This mixture is contacted with an olefin forming catalyst, preferably a SAPO molecular sieve catalyst, in a reaction zone or volume. The volume in which such contact takes place is herein termed the "reactor," which may be a part of a "reactor apparatus" or "reaction system." Another part of the reaction system may be a "regenerator," which comprises a volume wherein carbonaceous deposits (or coke) on the catalyst resulting from the olefin conversion reaction are removed by contacting the catalyst with regeneration medium.

The oxygenate that can be mixed with the alcohol from the hydration process of this invention comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof. The alcohols produced in this invention are suitable oxygenates and can be combined with another feed containing suitable oxygenates.

The method of making the preferred olefin product in this invention can include the additional step of making the oxygenate compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof. The preferred diluents are water and nitrogen. Water can be injected in either liquid or vapor form.

Hydrocarbons can also be included as part of the feedstock, i.e., as co-feed. As defined herein, hydrocarbons included with the feedstock are hydrocarbon compositions which are converted to another chemical arrangement when contacted with molecular sieve catalyst. These hydrocarbons can include olefins, reactive paraffins, reactive alkylaromatics, reactive aromatics or mixtures thereof. Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are a $C_4^+$ hydrocarbon mixtures, with the most preferred being $C_4^+$ hydrocarbon mixtures which are obtained from separation and recycle of reactor product.

In the process of this invention, coked catalyst can be regenerated by contacting the coked catalyst with a regeneration medium to remove all or part of the coke deposits. This regeneration can occur periodically within the reactor by ceasing the flow of feed to the reactor, introducing a regeneration medium, ceasing flow of the regeneration medium, and then reintroducing the feed to the fully or partially regenerated catalyst. Regeneration may also occur periodically or continuously outside the reactor by removing a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor.

Catalyst that has been contacted with feed in a reactor is defined herein as "feedstock exposed." Feedstock exposed catalyst will provide olefin conversion reaction products having substantially lower propane and coke content than a catalyst which is fresh and regenerated. A catalyst will typically provide lower amounts of propane as it is exposed to more feed, either through increasing time at a given feed rate or increasing feed rate over a given time.

At any given instant in time, some of the catalyst in the reactor will be fresh, some regenerated, and some coked or partially coked as a result of having not yet been regenerated. Therefore, various portions of the catalyst in the reactor will have been feedstock exposed for different periods of time. Since the rate at which feed flows to the reactor can vary, the amount of feed to which various portions of the catalyst can also vary. To account for this variation, the "average catalyst feedstock exposure index (ACFE index)" is used to quantitatively define the extent to which the entire catalyst in the reactor has been feedstock exposed.

As used herein, ACFE index is the total weight of feed divided by the total weight of molecular sieve (i.e., excluding binder, inerts, etc., of the catalyst composition) sent to the reactor. The measurement should be made over an equivalent time interval, and the time interval should be long enough to smooth out fluctuations in catalyst or feedstock rates according to the reactor and regeneration process step selected to allow the system to be viewed as essentially continuous. In the case of reactor systems with periodic regenerations, this can range from hours up to days or longer. In the case of reactor systems with substantially constant regeneration, minutes or hours may be sufficient.

Flow rate of catalyst can be measured in a variety of ways. In the design of the equipment used to carry the catalyst between the reactor and regenerator, the catalyst flow rate can be determined given the coke production rate in the reactor, the average coke level on catalyst leaving the reactor, and the average coke level on catalyst leaving the regenerator. In an operating unit with continuous catalyst flow, a variety of measurement techniques can be used.

In a preferred embodiment of this invention, only the molecular sieve in the catalyst sent to the reactor may be used in the determination of ACFE index. The catalyst sent to the reactor, however, can be either fresh or regenerated or a combination of both. Molecular sieve which may be recirculated to and from the reactor within the reactor apparatus (i.e., via ducts, pipes or annular regions), and which has not been regenerated or does not contain fresh catalyst, is not to be used in the determination of ACFE index.

In a preferred embodiment of this invention, a feed containing the oxygenates, and optionally a hydrocarbon, either separately or mixed with the oxygenates, is contacted with a catalyst containing a SAPO molecular sieve at process conditions effective to produce olefins in a reactor where the catalyst has an ACFE index of at least 1.0, preferably at least 1.5. An ACFE index in the range of 1.0 to 20 is effective, with a range of 1.5 to 15 being desirable. A range of 2 to 12 is particularly preferred.

Any standard reactor system can be used, including fixed bed, fluid bed or moving bed systems. Preferred reactors are co-current riser reactors and short contact time, countercurrent free-fall reactors. Desirably, the reactor is one in which the oxygenates can be contacted with a molecular sieve catalyst at a weight hourly space velocity (WHSV) of at least 1 $hr^{-1}$, preferably of from 1 $hr^{-1}$ to 1000 $hr^{-1}$, more preferably of from about 20 $hr^{-1}$ to 1000 $hr^{-1}$, and most preferably of from about 20 $hr^{-1}$ to 500 $hr^{-1}$. WHSV is defined herein as the weight of oxygenate, and hydrocarbon which may optionally be in the feed, per hour per weight of the molecular sieve content of the catalyst. Because the catalyst or the combined oxygenate feed stock may contain other materials which act as inerts or diluents, the WHSV is calculated on the weight basis of the oxygenate feed, and any hydrocarbon which may be present, and the molecular sieve contained in the catalyst.

Preferably, the combined oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range is from 200° C. to 700° C., preferably from 300° C. to 600° C., more preferably from 350° C. to 550° C. At the lower end of the temperature range, the formation of the desired olefin products may become markedly slow. At the upper end of the temperature range, the process may not form an optimum amount of product.

It is highly desirable to operate at a temperature of at least 300° C. and a Temperature Corrected Normalized Methane Sensitivity (TCNMS) of less than about 0.016. It is particularly preferred that the reaction conditions for making olefin from oxygenates comprise a WHSV of at least about 20 $hr^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T - 400)/400) \times 14.84)}$$

The pressure also may vary over a wide range, including autogenous pressures. Effective pressures may be in, but are not necessarily limited to, oxygenate partial pressures at least 1 psia, preferably at least 5 psia. The process is particularly effective at higher oxygenate partial pressures, such as an oxygenate partial pressure of greater than 20 psia. Preferably, the oxygenate partial pressure is at least 25 psia, more preferably at least 30 psia. For practical design purposes it is desirable to operate at a methanol partial pressure of not greater than 500 psia, preferably not greater than 400 psia, most preferably not greater than 300 psia.

The conversion of oxygenates to produce light olefins may be carried out in a variety of catalytic reactors. Reactor types include conventional reactors such as fixed bed reactors, fluid bed reactors, and riser reactors. These and other types of conventional reactors are known in the art. Preferred reactors are riser reactors.

In a preferred embodiment of the continuous operation, only a portion of the catalyst is removed from the reactor and sent to the regenerator to remove the accumulated coke deposits that result during the catalytic reaction. In the regenerator, the catalyst is contacted with a regeneration medium containing oxygen or other oxidants. Examples of other oxidants include $O_3$, $SO_3$, $N_2O$, $NO$, $NO_2$, $N_2O_5$, and mixtures thereof. It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, the coke deposits are removed from the catalyst during the regeneration process, forming a regenerated catalyst. The regenerated catalyst is then returned to the reactor for further contact with feed. Typical regeneration temperatures are FROM 250° C. to 700° C., desirably from 350° C. to 700° C. Preferably, regeneration is carried out from 450° C. to 700° C.

It is desirable to strip at least some of the volatile organic components which may be adsorbed onto the catalyst or located within its microporous structure prior to entering the regenerator. This can be accomplished by passing a stripping gas over the catalyst in a stripper or stripping chamber, which can be located within the reactor or in a separate vessel. The stripping gas can be any substantially inert medium that is commonly used. Examples of stripping gas are steam, nitrogen, helium, argon, methane, $CO_2$, CO, flue gas, and hydrogen.

It may be desirable to cool at least a portion of the regenerated catalyst to a lower temperature before it is sent back to the reactor. A heat exchanger located externally to the regenerator may be used to remove some heat from the catalyst after it has been withdrawn from the regenerator. When the regenerated catalyst is cooled, it is desirable to cool it to a temperature which is from 200° C. higher to 200° C. lower than the temperature of the catalyst withdrawn from the reactor. More desirably, it is cooled to a temperature from 10° C. to 200° C. lower than the temperature of the catalyst withdrawn from the reactor. This cooled catalyst then may be returned to either some portion of the reactor, the regenerator, or both. When the regenerated catalyst from the regenerator is returned to the reactor, it may be returned to the reactor's catalyst disengaging zone, the reaction zone, and/or the inlet zone. Introducing the cooled catalyst into the reactor or regenerator serves to reduce the average temperature in the reactor or regenerator.

In one embodiment, the reactor and regenerator are configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor.

It is preferred that the catalyst within the reactor have an average level of coke effective for selectivity to ethylene and/or propylene. Preferably, the average coke level on the catalyst will be from 2 wt. % to 30 wt. %, more preferably from 2 wt. % to 20 wt. %. In order to maintain this average level of coke on catalyst, the entire volume of catalyst can be partially regenerated under conditions effective to maintain the desired coke content on catalyst. It is preferred, however, to recycle only a portion of the coked catalyst for feed contact without regenerating. This recycle can be performed either internal or external to the reactor. The portion of coked catalyst to be regenerated is preferably regenerated under conditions effective to obtain a regenerated catalyst having a coke content of less than 2 wt. %, preferably less than 1.5 wt. %, and most preferably less than 1.0 wt. %.

In order to make up for any catalyst loss during the regeneration or reaction process, fresh catalyst can be added. Preferably, the fresh catalyst is added to the regenerated catalyst after it is removed from the regenerator, and then both are added to the reactor. However, the fresh catalyst can be added to the reactor independently of the regenerated catalyst. Any amount of fresh catalyst can be added, but it is preferred that an ACFE index of at least 1.5 be maintained.

A preferred embodiment of the present invention is shown in the FIGURE. In the FIGURE, ethylene monomer stream 1 is fed into polyethylene unit 2. The polyethylene unit includes a reactor and an polymer forming catalyst or free radical initiator to convert the ethylene monomer into polyethylene. The polyethylene unit 2 also includes a recycle loop, which circulates any unreacted ethylene monomer back into the polyethylene reactor. Polyethylene is withdrawn from the polyethylene unit as polyethylene stream 3.

A portion of the ethylene containing recycle stream is removed from the polyethylene unit 2, as purge stream 4. Purge stream 4 is feed into ethanol formation and recovery unit 7. Water stream 5 and a hydrating acid catalyst 6, are also feed into ethanol formation and recovery unit 7. Ethylene in the purge stream 4 is converted into ethanol in the ethanol formation and recovery unit. Impurities from the purge stream are withdrawn from the ethanol formation and recovery unit 7 in stream 8. Ethanol and water are removed from the ethanol formation and recovery unit 7 in stream 9. Stream 9 is then fed into oxygenate to olefin unit 11. Stream 10 a methanol feed is also fed into the oxygen olefin unit. The oxygenate to olefin unit converts the ethanol and methanol into olefin. The olefin leaves the oxygenate to olefin unit 11 as olefin containing stream 12. Olefin containing stream 12 is then fed into recovery section 13. The recovery section 13 separates the olefins and the by-products. The recovery section 13 includes a distillation column series that provides pure ethylene stream 14 pure propylene stream 15, and by-product stream 16. Ethylene stream 14 can now be circulated back into the polyethylene unit 2.

Having now fully described this invention, it will be appreciated by those skilled in the art that the invention can be performed within a wide range of parameters within what is claimed, without departing from the spirit and scope of the invention.

What is claimed is:

1. A method of producing olefins from oxygenates comprising:
   converting olefins in a purge stream in a polyolefin production process to an alcohol thereby producing an alcohol containing stream;
   mixing an oxygenate feed stream with the alcohol containing stream; and
   converting the mixed oxygenate feed stream and alcohol containing stream in the presence of an olefin forming catalyst to form an olefin product stream.

2. A method as claimed in claim 1 wherein the alcohol containing stream contains ethanol or propanol.

3. A method as claimed in claim 1 wherein the oxygenate feed is methanol.

4. A method as claimed in claim 1 wherein the olefin forming catalyst is a silicoaluminophosphate molecular sieve catalyst.

5. A method as claimed in claim 4 wherein the olefin product stream is used to produce polyolefins.

6. A method as claimed in claim 5 wherein impurities are removed during the polyolefin production process in a purge stream.

7. A method as claimed in claim 6 wherein the impurities in the purge stream comprise at least one compound selected from the group consisting of methane, ethane, butylenes, and hydrogen.

* * * * *